United States Patent [19]
Zelonis

[11] 4,110,078
[45] Aug. 29, 1978

[54] BINARY REAGENT SYSTEM FOR DETECTING DRUGS OF ABUSE

[76] Inventor: Paul Thomas Zelonis, 7926 Peak Point Ave., San Diego, Calif. 92126

[21] Appl. No.: 745,083

[22] Filed: Nov. 26, 1976

[51] Int. Cl.$^2$ .............. G01N 21/06; G01N 31/02; G01N 33/16
[52] U.S. Cl. .............. 23/230 R; 23/230 B; 252/408
[58] Field of Search .............. 23/230 B, 230 R; 252/408

[56] References Cited

U.S. PATENT DOCUMENTS

| | | | |
|---|---|---|---|
| 2,460,074 | 1/1949 | Davis | 252/408 |
| 2,520,993 | 9/1950 | Berger | 252/408 |
| 3,697,225 | 10/1972 | Schmitt | 23/253 TP |
| 3,713,779 | 1/1973 | Sirago | 23/259 |
| 3,761,227 | 9/1973 | Conrad | 23/230 B |
| 3,775,536 | 11/1973 | Spector | 424/1 |
| 3,799,741 | 3/1974 | Williams, Jr. | 23/230 B |
| 3,867,366 | 2/1975 | Rubenstein | 260/121 |
| 3,873,270 | 3/1975 | Hamilton | 23/230 B |
| 3,912,655 | 10/1975 | Shukla | 23/230 B |
| 3,915,639 | 10/1975 | Friedenberg | 23/230 B |
| 3,955,926 | 5/1976 | Fisher | 23/230 B |
| 3,963,421 | 6/1976 | Jones | 23/230 B |
| 3,966,410 | 6/1976 | Jahnsen | 23/230 B |
| 3,972,992 | 8/1976 | Cleeland, Jr. | 424/12 |

FOREIGN PATENT DOCUMENTS

1,388,221 3/1975 United Kingdom.

OTHER PUBLICATIONS

Abstract USSR 155,323 clg. (Non-Con), 22.6.62 (USSR) as 783,844, Pub. Nov. 1963, Shemyakin, F.M.
Abstract Russ 164,608 clg. (Non-Con), 13.3.63 (USSR) as 825,018, Pub. Feb. 1965, Shemyakin, F.M. et al.
K. Bailey, D.R. Gagne and R. K. Pike, "Identification of Some Analogs of the Hallucinogen Phencyclidine", J. Assoc. Official Analytical Chemists, 59 #1:81–89, 1976.
L. F. Small and R. E. Lutz, "Chemistry of the Opium Alkaloids", US Treasury Department, Public Health Service, Supplement No. 103 to the Public Health Reports, US Government Printing Office, Washington, 1932.

Primary Examiner—Sidney Marantz
Attorney, Agent, or Firm—Brown & Martin

[57] ABSTRACT

A binary reagent system for detecting drugs of abuse such as opium, heroin, phencyclidine, phencyclidine analogues, methadone and cocaine including a first reagent comprising chloroplatinic acid in aqueous solution and a second reagent comprising cobaltous thiocyanate in aqueous solution. Upon contacting a sample containing the drug with the reagent system, a characteristic coloration or precipitation is produced.

22 Claims, No Drawings

BINARY REAGENT SYSTEM FOR DETECTING DRUGS OF ABUSE

BACKGROUND OF THE INVENTION

Every year there is an increase in the use of drugs of abuse by the general population. Although experts have no appreciable difficulty in identifying most drugs in a well equipped laboratory, numerous situations occur where it is important to be able to detect common drugs of abuse outside the laboratory. Such situations occur frequently for law enforcement officers concerned with combatting illicit drug trade and use. Such persons need simple, rapid and specific methods for detecting drugs of abuse in the field. In addition, the methods of detection should be such that they can be performed by persons having minimum training.

Numerous reagents have been reported in the literature for detecting drugs of abuse (see for example, Arch. Toxikol., 25, 19(1969), J. Pharm. Sci., 56, 1526(1967)). Many of these reagents however are non-specific and/or give false positives when the suspected sample contains diluents and adulterants. Cobaltous thiocyanate, for example, is used as a color reagent for the detection of cocaine; however in excess of 50 other substances give a similiar color reaction with this reagent. Moreover, the testing of brown heroin with the recognized reagent for natural narcotics, i.e., the Marquis reagent (8–10 drops 40% formaldehyde/10 ml. concentrated sulfuric acid), has resulted in false positives due to the presence of dyes and pigments in the heroin samples. In addition, safety problems, such as acid spattering and the abrupt evolution of gases causing rupture of the sample container have been encountered in the field when reagents containing large amounts of strong acids were added to suspect liquid and powder samples.

Further, new smuggling techniques are constantly being developed by illegal drug traffikers which render many of the available field-test reagents useless or unreliable. Alcoholic solutions of pure cocaine, for example, cannot be meaningfully tested with either cobaltous thiocyanate or the Marquis reagent.

It would therefore be desirable to develop rapid, highly specific, non-hazardous methods for detecting the presence of drugs of abuse, which methods for detecting the presence of drugs of abuse, which methods could be easily performed in the field by persons having minimum training.

SUMMARY OF THE INVENTION

Accordingly, one aspect of the present invention relates to a highly specific binary reagent system for detecting drugs of abuse such as opium, heroin, phencyclidine, phencyclidine analogues, methadone and cocaine in suspect samples, whether liquid or solid in nature. More specifically, this aspect of the invention relates to a binary reagent system including a first reagent comprising chloroplatinic acid in aqueous solution and a second reagent comprising cobaltous thiocyanate in aqueous solution.

Another aspect of the present invention relates to a highly specific method for detecting the presence of the aforementioned drugs of abuse in liquids, powders and plant material. More specifically this aspect of the present invention relates to a rapid, selective, nonhazardous method for detecting the aforementioned drugs comprising, contacting the drug sample with the binary reagent of the invention in the presence of an organic solvent.

Still another aspect of the invention relates to a test kit for use in field tests for the rapid detection of the aforementioned drugs in solid and liquid samples. More specifically, this aspect of the invention relates to a test kit comprising three breakable vials, wherein the first vial contains an organic solvent, the second vial contains a reagent comprising chloroplatinic acid in aqueous solution and the third vial contains a reagent comprising cobaltous thiocyanate in aqueous solution.

Yet another aspect of the invention relates to methods for determining the presence and amount of diluents and/or adulterants present in samples suspected of containing drugs of abuse such as opium, heroin and cocaine.

Both chloroplatinic acid and cobaltous thiocyanate have been used singly and in combination with other reagents for detecting drugs of abuse (see U.S. Pat. Nos. 3,799,741, 3,912,655, 3,915,639, and 3,955,926). It has now been found however, that when chloroplatinic acid and cobaltous thiocyanate are used together, an unexpected increase in specificity can be obtained in detecting opium, heroin, phencyclidine, phencyclidine analogues, methadone and cocaine.

DETAILED DESCRIPTION OF THE INVENTION

A. Detection of Opium and Heroin

Opium the air-dried milky exudate obtained by incising the unripe capsules of Papaver Somniferum, contains approximately 10–16% morphine. Heroin, a diacetylmorphine, is commonly encountered in three forms: brown heroin, which is the less refined form; white heroin, which is the purified form; and white heroin which has been dyed brown.

During the past, difficulties have been encountered in the field in testing brown heroin due to the presence of dyes and pigments in the samples. Moreover current field tests fail to indicate the presence of diluents and some commonly encountered adulterants in heroin samples. In addition, no satisfactory field test exists for opium powder or gum as well as liquid solutions of heroin and/or opium.

Accordingly, a first preferred embodiment of the present invention is directed to the detection of heroin and opium, which detection avoids the aforementioned difficulties and disadvantages.

As mentioned previously, the binary reagent system of the invention broadly comprises a first reagent comprising chloroplatinic acid in aqueous solution and a second reagent comprising cobaltous thiocyanate in aqueous solution. More specifically, the binary reagent system for detecting the presence of opium and heroin further comprises a sufficient amount of an acid to provide the first reagent with a pH not greater than 4. Suitable acids that can be used include mineral acids, such as, for example, hydrochloric acid and sulfuric acid; organic acids, such as, for example, acetic acid; and mixtures of such acids. A mixture of acetic acid and hydrochloric acid is preferred. The first reagent contains from about 0.8 to 8 weight percent chloroplatinic acid (preferable about 4 weight percent) and the second reagent contains from about 0.5 to 4 weight percent cobaltous thiocyanate (preferably about 3 weight percent).

A preferred binary reagent system for detecting the presence of opium and heroin comprises:
(a) an aqueous solution prepared from the following components in the approximate parts by weight indicated:
   1 part chloroplatinic acid
   3 parts glacial acetic acid
   2.4 parts 12 N hydrochloric acid
   20 parts water; and
(b) an aqueous solution prepared from the following components in the approximate parts by weight indicated:
   3 parts cobaltous thiocyanate
   100 parts water.

Both solutions are preferably allowed to stand about 24 hours prior to use.

Broadly, the method of the invention for detecting the presence of opium and heroin comprises contacting the sample with a halogenated hydrocarbon and the binary reagent system previously discussed, and observing the color of the halogenated hydrocarbon layer, wherein the development of a clear green color in said layer indicates the presence of heroin and the development of a cloudy green color indicates the presence of opium in the sample. Suitable halogenated hydrocarbons that can be used include, for example, chloroform and methylene chloride. Although any sequence of addition may be employed, a preferred order of addition is solvent, followed by cobaltous thiocyanate reagent and then chloroplatinic acid reagent.

If the unknown to be analyzed is in a solid, generally nonparticulate form, it should be reduced to a powder before testing.

The preferred method of the invention for detecting the presence of opium and heroin is described herein below.

Approximately 0.01–0.05 parts of powder sample or 0.5–1 part of liquid sample is introduced into about 0.5–1 part of halogenated hydrocarbon. If the unknown sample contains sugars, the sugars will settle out in the bottom of the test container within 10 seconds. If sugars or other adulterants are not present the solution will be clear.

Thereafter, about 0.25–0.50 parts of the cobaltous thiocyanate reagent is introduced into the unknown mixture and the mixture is optionally agitated for approximately 5 seconds. If adulterants such as procaine are present in the sample, the top layer will turn an immediate bright blue color before agitation. Brown heroin will turn the bottom layer green upon agitation. White heroin will turn the bottom layer blue even if it is dyed brown. It is to be noted that other substances will also turn the bottom layer blue.

Thereafter, about 0.15–0.20 parts of the chloroplatinic acid reagent is added to the above obtained mixture and vigorous shaking is carried out for approximately 5 seconds. Brown heroin and white heroin will turn the bottom layer a clear emerald green color. Opium will turn the bottom layer a cloudy green color. A light green color with brown heroin roughly indicated a purity of less than 10%. A deep emerald (blackish) color roughly indicates a purity greater than 30%. It is to be noted that no appreciable color variation with purity is seen with white heroin.

The sensitivity of the above described method for powder samples is 5 mg. for opium, 1 mg. for white heroin and 0.5 mg. for brown heroin.

Approximately 175 controlled and non-controlled substances have been tested according to the above described method with only approximately 10 interferences. The interferring substances are either not normally encountered in illegal drug traffic or are inherent in heroin samples, e.g., acetylcodeine, thebaine and narcotine.

B. Detection of Phencyclidine, Phencyclidine Analogues and Methadone

In recent years, both phencyclidine and methadone have gained prominence in illicit drug traffic. Phencyclidine, i.e., 1-(1-phenylcyclohexyl) piperidine is a potent hallucinogen. Methadone, i.e., 6-dimethylamino-4,4-diphenyl-3-heptanone is a narcotic analgesic.

Presently no test exists for use in the field for the detection of either of these drugs of abuse. Accordingly, a second preferred embodiment of the present invention is directed to the detection of phencyclidine and methadone, which detection can be easily and rapidly performed in the field.

The binary reagent system for the detection of phencyclidine and methadone includes, in addition to the previously described first and second reagents, a sufficient amount of an acid to provide the first reagent with a pH not greater than 4. Suitable acids that can be used include mineral acids, such as, for example, hydrochloric acid and sulfuric acid; and organic acid, such as, for example, acetic acid. Acetic acid is preferred. The first reagent contains from about 0.8 to 8 weight percent chloroplatinic acid (preferably about 4 weight percent) and the second reagent contains from about 0.5 to 5 weight percent cobaltous thiocyanate (preferably about 2 weight percent).

A preferred binary reagent system for detecting the presence of phencyclidine and methadone comprises:
(a) an aqueous solution prepared from the following components in the approximate parts by weight indicated:
   1 part chloroplatinic acid
   5 parts glacial acetic acid
   20 parts water; and
(b) an aqueous solution prepared from the following components in the approximate parts by weight indicated:
   2 parts cobaltous thiocyanate
   63 parts glycerin
   50 parts water.

Both solutions are preferably allowed to stand about 24 hours prior to use.

Broadly the method of the invention for detecting the presence of phencyclidine and methadone comprises contacting the sample with the binary reagent system previously discussed and an aromatic hydrocarbon, and observing the color of the hydrocarbon layer, wherein the development of a clear intense blue color in said layer indicates the presence of phencyclidine and/or methadone in the sample. Suitable aromatic hydrocarbons that can be used include, for example, benzene, toluene and xylene. Benzene is preferred.

Although any sequence of addition may be employed, a preferable order of addition is chloroplatinic acid reagent, followed by cobaltous thiocyanate reagent and then aromatic hydrocarbon.

If the unknown to be analyzed is a solid, it should be reduced to powder before testing.

The preferred method of the invention for detecting the presence of phencyclidine and methadone is described herein below.

Approximately 0.01–0.02 parts of powder sample or 0.5–1 part of liquid sample is introduced into about 0.1–0.2 parts of the chloroplatinic acid reagent. Thereafter, about 0.25–0.75 parts of the cobaltous thiocyanate reagent is introduced into the unknown mixture and the mixture is gently agitated. After approximately 5 seconds of agitation, about 0.50–1.25 parts of aromatic hydrocarbon (preferably reagent grade benzene) are added to the unknown mixture and the mixture is shaken vigorously for about 5 seconds.

Powder and liquid samples containing phencyclidine and/or methadone will turn the hydrocarbon layer (i.e., the top layer) a deep clear blue. The color reaction obtained in all cases is stable for at least 24 hours if the test container is sealed to prevent evaporation. By this method, as little as 0.2 mg. of drug/sample can be detected.

The phencyclidine analogues, 1-(1-phenylcyclohexyl)pyrrolidine and 1-[1-(2-thienylcyclohexyl)]piperidine are also commonly encountered hallucinogens. Both of these analogues give a positive color reaction in the above described procedure.

Approximately 140 controlled and non-controlled substances have been tested according to the above described procedure with only three known interferences: propoxyphene, bromodiphenhydramine and chlorpromazine. These substances, however, are rarely, if ever, encountered in illicit drug traffic.

C. Detection of Cocaine

Cocaine, which occurs in the leaves of the coca bush (erythroxylon coca) is the methyl ester of benzoylecgonine. Because of the high incidence of addiction and associated toxicity, cocaine abuse is even more destructive in its consequences than morphine abuse.

Presently, no field test exists for suspected alcoholic or aqueous solutions of cocaine. Moreover, current tests fail to indicate the presence of diluents such as sugars, which are commonly encountered in cocaine samples.

Accordingly, a third preferred embodiment of the present invention is directed to the detection of cocaine, which detection overcomes the deficiencies of the prior art.

The binary reagent system for the detection of cocaine includes, in addition to the previously described first and second reagents, a sufficient amount of a mineral acid to provide the first reagent with a pH not greater than 4, said first reagent further comprising sodium bromide; and a sufficient amount of an organic acid to provide the second reagent with a pH not greater than 4. Suitable mineral acids that can be used include, for example, phosphoric acid and hydrochloric acid (phosphoric acid being preferred). Suitable organic acids that can be used include, for example, acetic acid and the like. Acetic acid is preferred. The first reagent contains from about 0.8 to 8 weight percent chloroplatinic acid (preferable about 4 weight percent) and from about 7 to 11 weight percent sodium bromide (preferable about 9 weight percent). The second reagent contains from about 0.6 to 2.5 weight percent cobaltous thiocyanate (preferable about 1 weight percent).

A preferred binary reagent system for detecting the presence of cocaine comprises:

(a) an aqueous solution prepared from the following components in the approximate parts by weight indicated:
   5 parts chloroplatinic acid
   10 parts sodium bromide
   20 parts aqueous phosphoric acid (85%)
   80 parts water; and (b) an aqueous solution prepared from the following components in approximate parts by weight indicated:
   0.8 parts cobaltous thiocyanate
   26 parts glacial acetic acid
   20 parts ethanol
   50 parts water.

Both solutions are preferably allowed to stand about 24 hours prior to use.

Broadly, the method of the invention for detecting the presence of cocaine comprises contacting the sample with a halogenated hydrocarbon and the binary reagent system previously discussed and observing the mixture for the formation of a granular precipitate. Suitable halogenated hydrocarbons that can be used, include, for example, chloroform and methylene chloride. Although any sequence of addition may be employed, a preferred order of addition is solvent, followed by chloroplatinic acid reagent and then cobaltous thiocyanate reagent.

If the unknown sample to be analyzed is in a solid, generally nonparticulate form, it should be reduced to a powder before testing.

The preferred method of the invention for detecting the presence of cocaine is described herein below.

Approximately 0.03–0.04 parts of powder sample or 0.5–1 part of liquid sample is introduced into about 0.5–1.5 parts of halogenated hydrocarbon. If the sample is pure cocaine, the cocaine dissolves almost completely within one minute. If the sample has been adulterated with a sugar, such as mannitol, the sugar will settle to the bottom of the test container thereby affording a visual estimation of the amount of adulterant present.

Thereafter, approximately 0.1–0.2 parts of the chloroplatinic acid reagent is introduced into the unknown mixture. If the suspect sample is a powder, the appearance of red colored particles on the surface of the aqueous layer indicates the presence of adulterants in the sample.

Approximately 0.5–2 parts of cobaltous thiocyanate reagent is then introduced into the unknown mixture and the mixture is agitated vigorously for about 5 seconds. Following agitation, two distinct layers are observed, i.e., a clear aqueous top layer and a bottom layer of halogenated hydrocarbon containing a swirling precipitate. The color of the precipitate may vary, however, it is to be emphasized that the detection of cocaine according to the instant invention is based on precipitate formation independent of color. Approximately 5 seconds after the appearance of the two layers, the swirling precipitate begins to form a sediment and a blue-green supernatant halogenated hydrocarbon layer appears between the sediment and the aqueous layer. It should be noted that the purity of the unknown sample is directly proportional to the amount of precipitate formed and inversely proportional to the size of the blue-green halogenated hydrocarbon supernatant.

The quantities of cocaine detectable in the above described method are about 6 mg. drug/ml. liquid sample and 1 mg. drug in a powder sample.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE I

Approximately 5 mg. of white heroin is added to 0.5 ml. of chloroform in a test vial. A clear solution is obtained indicating the absence of insoluable adulterants. Thereafter, 0.25 ml. of aqueous cobaltous thiocyanate solution (stock solution prepared from 3 g. of cobaltous thiocyanate and 100 ml. water) is added to the test vial and the vial is agitated for about 5 seconds and then allowed to stand for a color change to develop. In several seconds the chloroform layer develops a blue color which characteristic of white heroin. Thereafter, 0.15–0.20 ml. of aqueous chloroplatinic acid solution (stock solution prepared from 1 g. chloroplatinic acid, 3 ml. glacial acetic acid, 2 ml. 12 N hydrochloric acid and 20 ml. water) is added to the test vial and the vial is shaken vigorously for about 5 seconds and then allowed to stand for several seconds. The chloroform layer develops a clear emerald green color which is characteristic of heroin.

Repeating the above procedure using an equivalent amount of opium results in the development of a cloudy green color in the chloroform layer which is characteristic of opium.

EXAMPLE II

Approximately 5 mg. of phencyclidine is added to a test vial containing 0.15 ml. of aqueous chloroplatinic acid solution (stock solution prepared from 1 g. chloroplatinic acid, 5 ml. glacial acetic acid and 20 ml. water). Thereafter, 0.5 ml. of aqueous cobaltous thiocyanate solution (stock solution prepared from 2 g. cobaltous thiocyanate, 50 ml. glycerin and 50 ml. water) is added to the test vial and the vial is gently agitated. After about 5 seconds of agitation, 1 ml. of benzene is added to the vial and vigorous agitation is carried out for about 5 seconds. The mixture is then allowed to stand for a color change to develop. In several seconds the benzene layer develops a deep clear blue color.

Repeating the above procedure using an equivalent amount of methadone or a phencyclidine analogue, i.e., 1-(1-phenylcyclohexyl)pyrrolidine or 1-[1-(2-thienylcyclohexyl)]piperidine also results in the development of a deep clear blue color in the benzene layer.

EXAMPLE III

Approximately 15 mg. of cocaine is added to 1 ml. of chloroform in a test vial. A clear suspension is obtained indicating the absence of adulterants. Thereafter, 0.15 ml. of aqueous chloroplatinic acid solution (stock solution prepared from 5 g. chloroplatinic acid, 10 g. sodium bromide, 12 ml. phosphoric acid (85%), and 80 ml. water) is added to the test vial and the vial is gently agitated for several seconds. Approximately 1 ml. of aqueous cobaltous thiocyanate, (stock solution prepared from 0.8 ml. cobaltous thiocyanate, 25 ml. glacial acetic acid, 25 ml. ethanol and 50 ml. water) is then added to the vial and vigorous agitation is carried out for about 5 seconds. About 5 seconds after agitation the mixture separates into two distinct layers, i.e., a clear aqueous top layer and a bottom layer containing a swirling precipitate which is characteristic for cocaine. After about 5 minutes, the precipitate begins to settle and a blue-green chloroform supernatant layer forms between the sediment and the aqueous top layer. This blue-green layer becomes more pronounced with time.

EXAMPLE IV

A test kit according to the instant invention for the detection of the aforementioned drugs of abuse consists of 3 breakable glass vials which contain solvent, aqueous chloroplatinic acid solution and aqueous cobaltous thiocyanate solution respectively.

Each vial, approximately 4–5 cm. in length and about 0.5 cm. in diameter, is sealed at both ends. The vials, made of thin glass which can be readily broken to release the liquid contents, are conveniently packaged in a small plastic case suitable for carrying in the field. The case can also serve as a test container when made of inert plastic.

Details of the test kit used for the detection of opium, heroin, phencyclidine, phencyclidine analogues, methadone and cocaine are given in the following table.

| DRUG | VIAL 1 | VIAL 2 | VIAL 3 |
| --- | --- | --- | --- |
| Opium and Heroin | 0.5 – 1 ml. chloroform or methylene chloride | 0.15 – 0.20 ml. aqueous chloroplatinic acid solution formulated as set forth in Example I | 0.25 – 0.5 ml. aqueous cobaltous thiocyanate reagent formulated as set forth in Example I |
| Phencyclidine, Phencyclidine Analogues and Methadone | 0.5 – 1.25 ml benzene, toluene or xylene | 0.1 – 0.2 ml. aqueous chloroplatinic acid solution formulated as set forth in Example II | 0.25 – 0.75 ml. aqueous cobaltous thiocyanate solution formulated as set forth in Example II |
| Cocaine | 0.5 – 1.5 ml. chloroform or methylene chloride | 0.1 – 0.2 ml. aqueous chloroplatinic acid solution formulated as set forth in Example III | 0.5 – 2 ml. aqueous cobaltous thiocyanate solution formulated as set forth in Example III |

I claim:

1. A highly specific binary reagent system for detecting the presence, in a sample, of a drug of abuse selected from the group consisting of opium, heroin, phencyclidine, phencyclidine analogues, methadone and cocaine, comprising:
   (a) a first reagent comprising chloroplatinic acid in aqueous solution;
   (b) a second reagent comprising cobaltous thiocyanate in aqueous solution, and
   (c) a hydrocarbon liquid.

2. A binary reagent system of claim 1 for detecting the presence of opium or heroin further comprising sufficient amount of an acid to provide said first reagent with a pH not greater than 4.

3. A binary reagent system of claim 2 wherein said first reagent comprises from 0.8 to 8 weight percent chloroplatinic acid and wherein said second reagent comprises from 0.5 to 4 weight percent cobaltous thiocyanate.

4. A binary reagent system for detecting the presence of opium or heroin comprising:
   (a) an aqueous solution prepared from the following components in the approximate parts by weight indicated:
   1 part chloroplatinic acid
   3 parts glacial acetic acid
   2.4 parts 12 N hydrochloric acid
   20 parts water; and
   (b) an aqueous solution prepared from the following components in the approximate parts by weight indicated:
   3 parts cobaltous thiocyanate
   100 parts water.

5. A binary reagent system of claim 1 for detecting the presence of phencyclidine, phencyclidine analogues and methadone, further comprising sufficient acid to provide said first reagent with a pH not greater than 4.

6. A binary reagent system of claim 5 wherein said first reagent comprises from 0.8 to 8 weight percent chloroplatinic acid and wherein said second reagent comprises 0.5 to 5 weight percent cobaltous thiocyanate.

7. A binary reagent system for detecting the presence of phencyclidine, phencyclidine analogues and methadone, comprising:
   (a) an aqueous solution prepared from the following components in the approximate parts by weight indicated:
   1 part chloroplatinic acid
   5 parts glacial acetic acid
   20 parts water; and
   (b) an aqueous solution prepared from the following components in the approximate parts by weight indicated:
   2 parts cobaltous thiocyanate
   63 parts glycerin
   50 parts water.

8. A binary reagent system of claim 1 for detecting the presence of cocaine, further comprising:
   (a) a sufficient amount of a mineral acid to provide said first reagent with a pH not greater than 4, said first reagent further comprising sodium bromide; and
   (b) a sufficient amount of a organic acid to provide said second reagent with a pH not greater than 4.

9. A binary reagent system of claim 8 wherein said first reagent comprises from 0.8 to 8 weight percent chloroplatinic acid and from 7 to 11 weight percent sodium bromide and wherein said second reagent comprises from 0.6 to 2.5 weight percent cobaltous thiocyanate.

10. A binary reagent system for detecting the presence of cocaine, comprising:
   (a) an aqueous solution prepared from the following components in the approximate parts by weight indicated:
   5 parts chloroplatinic acid
   10 parts sodium bromide
   20 parts aqueous phosphoric acid (85%)
   80 parts water; and
   (b) an aqueous solution prepared from the following components in the approximate parts by weight indicated:
   0.8 parts cobaltous thiocyanate
   26 part glacial acetic acid
   20 parts ethanol
   50 parts water.

11. A highly specific colorimetric method for detecting the presence of opium and heroin in a sample, which comprises:
   (1) contacting said sample with
      (a) a halogenated hydrocarbon;
      (b) a first reagent comprising chloroplatinic acid in aqueous solution; and
      (c) a second reagent comprising cobaltous thiocyanate in aqueous solution; and
   (2) observing the color of the halogenated hydrocarbon layer, wherein the development of a cloudy green color in said layer indicated the presence of opium and the development of a clear emerald color in said layer indicates the presence of heroin in said sample.

12. The method of claim 11 further comprising a sufficient amount of an acid to provide said first reagent with a pH not greater than 4.

13. The method of claim 12 wherein said first reagent comprises from 0.8 to 8 weight percent chloroplatinic acid and wherein said second reagent comprises from 0.5 to 4 weight percent cobaltous thiocyanate.

14. The method of claim 13 which comprises:
   (a) contacting 0.01–1.0 part of said sample with 0.5–1.0 of halogenated hydrocarbon;
   (b) contacting the mixture obtained in (a) above with 0.25–0.50 parts of a reagent comprising about 3 parts of cobaltous thiocyanate and 100 parts water;
   (c) contacting the mixture obtained in (b) above with 0.15–0.20 parts of a reagent comprising about 1 chloroplatinic acid, 3 parts glacial acetic acid, 2.4 parts 12 N hydrochloric acid and 20 parts water; and
   (d) observing the color of the halogenated hydrocarbon layer in the mixture obtained in (c) above.

15. A highly specific colorimetric method for detecting the presence of phencyclidine, phencyclidine analogues, and methadone in a sample, which comprises:
   (1) contacting said sample with:
      (a) a first reagent comprising chloroplatinic acid in aqueous solution;
      (b) a second reagent comprising cobaltous thiocyanate in aqueous solution; and
      (c) an aromatic hydrocarbon; and
   (2) observing the color of the hydrocarbon layer wherein the development of a clear intense blue color in said layer indicates the presence of phencyclidine, phencyclidine analogues or methadone in said sample.

16. The method of claim 15 further comprising a sufficient amount of an acid to provide said first reagent with a pH not greater than 4.

17. The method of claim 16 wherein said first reagent comprises from 0.8 to 8 weight percent chloroplatinic acid and wherein said second reagent comprises from 0.5 to 5 weight percent cobaltous thiocyanate.

18. The method of claim 17 which comprises:
   (a) contacting 0.01–1 part of said sample with 0.1–0.2 parts of a reagent comprising about 1 part chloroplatinic acid, 5 parts glacial acetic acid and 20 parts water;

(b) intimately contacting the mixture obtained in (a) above with 0.25–0.75 parts of a reagent comprising about 2 parts cobaltous thiocyanate, 63 parts glycerin and 50 parts water;

(c) intimately contacting the mixture obtained in (b) above with 0.5–1.25 parts of aromatic hydrocarbon; and (d) observing the color of the hydrocarbon layer in the mixture obtained in (c) above.

19. A highly specific precipitation method for detecting the presence of cocaine in a sample, which comprises:

(1) contacting said sample with
  (a) a halogenated hydrocarbon;
  (b) a first reagent comprising chlorplatinic acid and sodium bromide in aqueous solution; and
  (c) a second reagent comprising cobaltous thiocyanate in aqueous solution; and (2) observing the mixture obtained in (1) above wherein the development of a granular precipitate indicates the presence of cocaine in said sample.

20. The method of claim 19 further comprising:
  (a) a sufficient amount of a mineral acid to provide said first reagent with a pH not greater than 4; and
  (b) a sufficient amount of an organic acid to provide said second reagent with a pH not greater than 4.

21. The method of claim 20 wherein said first reagent comprises from 0.8 to 8 weight percent chloroplatinic acid and from 7 to 11 weight percent sodium bromide and wherein said second reagent comprises from 0.6 to 2.5 weight percent cobaltous thiocyanate.

22. The method of claim 21 which comprises:
  (a) contacting 0.03 to 1 part of said sample with 0.5–1.5 parts of halogenated hydrocarbon;
  (b) intimately contacting the mixture obtained in a) above with 0.1–0.2 parts of a reagent comprising about 5 parts chloroplatinic acid, 10 parts sodium bromide, 20 parts aqueous phosphoric acid (85%) and 80 parts water;
  (c) intimately contacting the mixture obtained in b) above with 0.5–2 parts of a reagent comprising about 0.8 part cobaltous thiocyanate, 26 parts glacial acetic acid, 20 parts ethanol and 50 parts water; and
  (d) observing the mixture obtained in c) above for precipitate formation.

* * * * *